(12) United States Patent
DeStefano et al.

(10) Patent No.: US 7,914,770 B2
(45) Date of Patent: Mar. 29, 2011

(54) FORMULATION FOR A METERED DOSE INHALER USING HYDRO-FLUORO-ALKANES AS PROPELLANTS

(75) Inventors: George DeStefano, Brookfield, CT (US); Linda Jean Kelash-Cannavo, Newtown, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 1038 days.

(21) Appl. No.: 10/804,710

(22) Filed: Mar. 19, 2004

(65) Prior Publication Data

US 2004/0184994 A1    Sep. 23, 2004

Related U.S. Application Data

(60) Provisional application No. 60/456,113, filed on Mar. 20, 2003.

(51) Int. Cl.
*A61K 9/12* (2006.01)
(52) U.S. Cl. .......................................... 424/45; 424/46
(58) Field of Classification Search ............... 424/45, 424/46
See application file for complete search history.

(56) References Cited

U.S. PATENT DOCUMENTS

| | | | |
|---|---|---|---|
| 5,225,183 A | 7/1993 | Purewal et al. | |
| 5,682,875 A | 11/1997 | Blower et al. | |
| 5,836,299 A | 11/1998 | Kwon | |
| 5,919,435 A | 7/1999 | Taylor et al. | |
| 6,036,942 A | 3/2000 | Alband | |
| 6,045,778 A | 4/2000 | Jager et al. | |
| 6,092,696 A | 7/2000 | Thomas | |
| 6,234,362 B1 | 5/2001 | Thomas | |
| 6,261,539 B1 | 7/2001 | Adjei et al. | |
| 6,305,371 B1 | 10/2001 | Frid et al. | |
| 6,306,368 B1 | 10/2001 | Taylor et al. | |
| 6,423,298 B2 * | 7/2002 | McNamara et al. | 424/45 |
| 6,475,467 B1 * | 11/2002 | Keller et al. | 424/45 |
| 6,511,652 B1 * | 1/2003 | Ashurst et al. | 424/45 |
| 2001/0031244 A1 | 10/2001 | Lewis et al. | |
| 2003/0066525 A1 | 4/2003 | Lewis et al. | |
| 2003/0089368 A1 | 5/2003 | Zhao | |
| 2003/0089369 A1 | 5/2003 | Lewis et al. | |
| 2003/0190287 A1 | 10/2003 | Lewis et al. | |
| 2003/0206870 A1 | 11/2003 | Lewis et al. | |

FOREIGN PATENT DOCUMENTS

| | | |
|---|---|---|
| EP | 1219293 A2 | 3/2002 |
| EP | 1219293 A3 | 3/2002 |
| EP | 1241113 | 9/2002 |
| WO | WO 9413262 * | 6/1994 |
| WO | WO 95/02651 | 1/1995 |
| WO | WO 97/01611 | 1/1997 |
| WO | WO 98/56349 | 12/1998 |
| WO | WO 00/30607 | 6/2000 |
| WO | WO 00/30608 | 6/2000 |
| WO | WO 03/002169 | 1/2003 |

OTHER PUBLICATIONS

Robert O. Williams III and Chengjiu Hu, Influence of Water on the Solubility of Two Steroid Drugs in Hydrofluoro-alkane (HFA) Propellants,—Research Paper—Drug Development and Industrial Pharmacy 27(1), 71-79 (2001).

* cited by examiner

*Primary Examiner* — Mina Haghighatian
(74) *Attorney, Agent, or Firm* — Michael P. Morris; Anthony P. Bottino

(57) ABSTRACT

An improved suspension formulation for use in a metered-dose inhaler having a hydro-fluoro-alkane propellant is described, the improvement being the controlled addition of a small quantity of water.

11 Claims, No Drawings

FORMULATION FOR A METERED DOSE INHALER USING HYDRO-FLUORO-ALKANES AS PROPELLANTS

APPLICATION DATA

This application claims benefit to U.S. provisional application No. 60/456,113 filed Mar. 20, 2003.

BACKGROUND OF THE INVENTION

The physical stability (particle size growth, flocculation rate, sedimentation/creaming behaviors) of a non-aqueous based suspension metered dose inhaler (MDI) formulation is a critical factor that affects the pharmaceutical performance characteristics of the drug product. For a suspension MDI, the key pharmaceutical performance characteristics of the formulation include reproducible dosing, ready dispersibility of the suspended medicament, and minimal particle size change over time.

Water has long been considered to have a negative impact on the physical stability of non-aqueous suspensions. In the literature, the following two aspects are well established:
a) too much water results in altered sedimentation characteristics leading to fast sedimentation and therefore to variability in dose of the suspended active ingredient, and
b) too much water can alter the particle size distribution by contributing to the formation of flocculates and aggregates of the individual drug particles or can cause solubilizing and re-crystallizing of drug particles.

SUMMARY OF THE INVENTION

It is therefore an object to provide a formulation wherein the amount of water is about 0.13 to about 0.18 percent (w/w) of the product formulation.

It is another object of the invention to provide a meter dose inhaler containing the formulation according to the invention.

It is yet another object of the invention to provide a process of making a formulation according to the invention.

DETAILED DESCRIPTION OF THE PREFERRED EMBODIMENTS

The inventors have determined that a minimum amount of water is needed to ensure adequate re-dispersion of the suspended active ingredient. The term "product formulation" shall be understood to mean all components as described herein contained in the metered dose inhaler. It shall be appreciated by the skilled artisan that this amount of water (w/w) of the product formulation is the final volume, and that one or more of the components may already possess water. The amount of water to add to achieve the desired amount in the product formulation can be determined without undue experimentation by those of ordinary skill in the art from the teachings in this application and from methods known in the art. Preferably, the amount of water is 0.16% w/w of the product formulation. In this case, it has been found by the inventors of this application that adding about 0.13% or 0.14% of water to the other components as shown in the tables below achieves the preferred amount.

If the active ingredient is not readily re-dispersible, then, after a period of non-use by the patient, the amount of active ingredient per actuation will not be on target (either super-potent or sub-potent). The addition of specific amounts of water can aid in the ready re-dispersibility of the active ingredient in the metering chamber. This finding has been established for a suspension/solution formulation for use in a metered dose inhaler using an hydro-fluoro-alkane (HFA) as propellant. Specifically, a formulation comprising albuterol sulfate and ipratropium bromide, together with various other excipients and carriers, is described, using the HFA known in the industry as 134a.

Suitable excipients will be apparent to those of ordinary skill in the art. These include, but are not limited to: organic acids such as citric acid, lubricants such as oleic acid, ethanol and carriers.

Suitable carriers will be apparent to those of ordinary skill in the art. These include, but are not limited to: soy lecithin, polyvinylpyrollidones, organic polymers, phospholipids.

There are various MDI publications in the literature including US Publications 2003/0066525, 2003/0089368, US2001031244, US2003089369, US2003190287, US2003206870, U.S. Pat. Nos. 5,225,183, 5,919,435, 6,306,368, 5,836,299, 6,092,696, 6,234,362, 6,036,942, 5,682,875, 6,305,371, and PCT publications WO 95/02651, WO 97/01611, WO 03/002169, WO 00/30607, WO 00/30608 and WO 98/56349 and EP 1 241 113, many deal with all aspects of HFA formulations. The inventors are not aware of any formulation patent publications for suspension MDIs that requires or recommends water to be added to the formulation to enhance performance.

Therefore, in one embodiment there is provided:

a formulation comprising water in an amount of about 0.13 to about 0.18 percent (w/w) of the product formulation, at least one HFA as a propellant, one or more active ingredients, and one or more excipients.

In another embodiment there is provided:

a formulation comprising water in an amount of about 0.13 to about 0.18 percent (w/w) of the product formulation, at least one HFA as a propellant, albuerol sulfate, ipratropium bromide, and one or more excipients.

Below are three tables showing formulations incorporating the invention, that is, the deliberate addition of water to a formulation to be used in an MDI using at least one HFA as a propellant. The first two tables provide specific details for such formulation having albuerol sulfate and ipratropium bromide as active ingredients. The first table provides the formulation with no canister overfill.

TABLE 1

| COMPONENT | MASS PER CAN | PERCENT |
|---|---|---|
| Albuterol Sulphate (micronized) | 0.0240 g | 0.208 |
| Ipratropium Bromide (monohydrate) | 0.0042 g | 0.036 |
| Ethanol (dehydrated, USP) | 1.153 g | 10 |
| Water | 0.0150 g | 0.13 |
| Polyvinylpyrrolidone (PVP, K-25) | 0.0058 g | 0.050 |
| Citric Acid (anhydrous) | 0.0005 g | 0.004 |

TABLE 1-continued

| COMPONENT | MASS PER CAN | PERCENT |
| --- | --- | --- |
| HFA 134a (1,1,1,2-tetrafluoroethane) | 10.3285 g | 89.542 |
| TOTAL | 11.5310 g | 100 |

The second table provides the same albuterol sulfate and ipratropium bromide formulation with a projected canister overfill included.

TABLE 2

| COMPONENT | MASS PER CAN | PERCENT |
| --- | --- | --- |
| Albuterol Sulphate (micronized) | 0.0309 g | 0.208 |
| Ipratropium Bromide (monohydrate) | 0.0054 g | 0.036 |
| Ethanol (dehydrated, USP) | 1.482 g | 10 |
| Water | 0.0193 g | 0.13 |
| Polyvinylpyrrolidone (PVP, K-25) | 0.0074 g | 0.050 |
| Citric Acid (anhydrous) | 0.0006 g | 0.004 |
| HFA 134a (1,1,1,2-tetrafluoroethane) | 13.2744 g | 89.542 |
| TOTAL | 14.82 g | 100 |

The third table provides expected ranges for an albuterol sulfate/ipratropium bromide formulation according to the present invention.

TABLE 3

| COMPONENT | MASS PER CAN | PERCENT |
| --- | --- | --- |
| Albuterol Sulphate (micronized) | 0.0240 g<br>0.0216–0.0264<br>(+/−10%) | 0.208 |
| Ipratropium Bromide (monohydrate) | 0.0042 g<br>0.0038–0.0046<br>(+/−10%) | 0.036 |
| Ethanol (dehydrated, USP) | 1.153 g | 10 |
| Polyvinylpyrrolidone (PVP, K-25) | 0.0058 g<br>0.0049 g–0.0067 g<br>(+/−15%) | 0.050 |
| Citric Acid (anhydrous) | 0.0005 g | 0.004 |
| HFA 134a (1,1,1,2-tetrafluoroethane) and/or HFA 227 | 10.325 g | 89.542 |
| TOTAL | 11.5125 g | 100 |

This invention will provide a solution to the problem of actuation variability in formulations used in MDIs having at least one HFA as propellant where:
 a) the formulation has a suspended, solid medicament and
 b) the valve is designed to include a metering chamber, that is an area for the formulation to be dosed or dispensed to reside between actuations or dosings.

Provided these two conditions are met, there is the potential that the addition of a small, controlled amount of water can improve the redispersibility of the formulation in the metering chamber. This possibility exists regardless of whether the formulation is a "pure" suspension, that is, no drug or active ingredient is dissolved in the formulation. This possibility is also independent of the solid medicament, the stabilizing agent (if one is used), the propellants used or the type of co-solvent, if any, used.

Therefore, in another embodiment of the invention, there is provided a metered dose inhaler comprising
 a formulation as described herein above wherein the albuterol sulfate, and the ipratropium bromide of the formulation is suspended;
 a valve containing a metering chamber that is an area for the formulation to be dosed or dispensed to reside between actuations or dosings.

In yet another embodiment of the invention, there is provided a process of making a formulation as desribed herein above, comprising:
 preparing a concentrate by adding:
  ethanol, citric acid, ipratropium bromide monohydrate, polyvinylpyrrolidone and albuterol sulfate;
 preparing a propellant, ethanol and water mixture, said mixture containing:
  propellant HFA 134a,
  a mixture of ethanol and water;
 adding the concentrate to the mixture of propellant-ethanol-water to provide the formulation.

A formulation according to the present invention can be made as follows:
1. Concentrate Preparation
   Prepare Concentrate with:
    Ethanol,
    Citric acid
    Ipratropium bromide monohydrate
    PVP
    Albuterol Sulfate
   Do not add water.
2. Dispensing of Propellant, Ethanol and Water
   Charge Formulation Vessel with:
    Propellant HFA 134a
    Mixture of ethanol/water
   Concentration of Formulation at this Process Step:

| | |
| --- | --- |
| Propellant | 95.45% |
| Ethanol | 4.38% |
| Water | 0.17% |

3. Final Product Formulation
   Add concentrate (from Step 1) to the mixture of propellant-ethanol-water Concentration of Formulation at this Process Step:

| | |
| --- | --- |
| Propellant | 89.84% |
| Ethanol | 10.00% |
| Water | 0.16% |
| Actives | negligible |
| PVP | negligible |
| Citric acid | negligible |

All publications cited in this application are incorporated herein by reference in their entirety.

What is claimed is:

1. A formulation comprising water in an amount of 0.13 to about 0.18 percent (w/w) of the product formulation, at least one HFA as a propellant,
   one or more excipients, and
   active ingredients albuterol sulfate and ipratropium bromide wherein the active ingredients of the formulation are suspended.

2. The formulation according to claim 1 wherein the amount of water is 0.13 to 0.16% w/w of the product formulation.

3. The formulation according to claim 1 wherein the HFA propellant is HFA 134a.

4. The formulation according to claim 3 wherein the excipients are ethanol, citric acid and polyvinylpyrrolidone.

5. A metered dose inhaler comprising
a formulation according to claim 1;
a valve containing a metering chamber that is an area for the formulation to be dosed or dispensed to reside between actuations or dosings.

6. A process of making a formulation according to the claim 5 comprising:
preparing a concentrate by adding:
ethanol, citric acid, ipratropium bromide monohydrate, polyvinylpyrrolidone and albuterol sulfate;
preparing a propellant, ethanol and water mixture, said mixture containing:
propellant HFA 134a,
a mixture of ethanol and water;
adding the concentrate to the mixture of propellant-ethanol-water to provide the formulation.

7. The formulation according to claim 4, wherein the formulation is in a metered dose inhaler comprising a valve containing a metering chamber that is an area for the formulation to be dosed or dispensed to reside between actuations or dosings.

8. A metered dose inhaler comprising
a formulation according to claim 2;
a valve containing a metering chamber that is an area for the formulation to be dosed or dispensed to reside between actuations or dosings.

9. A metered dose inhaler comprising
a formulation according to claim 3;
a valve containing a metering chamber that is an area for the formulation to be dosed or dispensed to reside between actuations or dosings.

10. A metered dose inhaler comprising
a formulation according to claim 4;
a valve containing a metering chamber that is an area for the formulation to be dosed or dispensed to reside between actuations or dosings.

11. The formulation according to claim 1, wherein the water amount is 0.16 percent (w/w) of the product formulation.

* * * * *